United States Patent [19]

Wolff et al.

[11] Patent Number: 4,833,161

[45] Date of Patent: May 23, 1989

[54] CARBOXYLIC ACID DERIVATIVES AND PHARMACEUTICAL COMPOSITIONS AND USES

[75] Inventors: Hans P. Wolff, Hirschberg-Grossachsen; Hans-Frieder Kühnle, Weinheim, both of Fed. Rep. of Germany

[73] Assignee: Boehringer Mannheim GmbH, Mannheim, Fed. Rep. of Germany

[21] Appl. No.: 141,312

[22] Filed: Jan. 6, 1988

[30] Foreign Application Priority Data

Jan. 13, 1987 [DE]  Fed. Rep. of Germany ....... 3700732

[51] Int. Cl.$^4$ .................... A61K 31/38; C07D 409/00; C07D 333/36
[52] U.S. Cl. .................................. 514/445; 514/438; 514/444; 514/447; 549/59; 549/63; 549/65; 549/66; 549/68; 549/77; 549/79
[58] Field of Search .............. 514/438, 444, 445, 447; 549/59, 63, 65, 66, 68, 77, 79

[56] References Cited

U.S. PATENT DOCUMENTS 4,621,098 11/1986 Umminger et al. ................. 562/429
4,730,005 3/1988 Gleason .............................. 562/429

FOREIGN PATENT DOCUMENTS 2709504 9/1977 Fed. Rep. of Germany ........ 549/79

Primary Examiner—Alan Siegel
Attorney, Agent, or Firm—Felfe & Lynch

[57] ABSTRACT

The present invention provides carboxylic acid derivatives of the general formula:

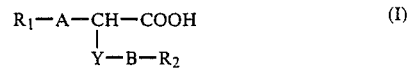

wherein $R_1$ and $R_2$, which can be the same or different, are optionally substituted aryl radicals or optionally substituted heterocyclic radicals, A is a straight-chained or branched, saturated or unsaturated alkylene chain containing up to 10 carbon atoms which can contain an oxygen, sulphur or nitrogen atom and is optionally substituted by a hydroxyl group, Y is an $S(O)_n$ group or an oxygen atom, n is 0, 1 or 2 and B is a valency bond or a saturated or unsaturated alkylene radical containing up to 5 carbon atoms; as well as the physiologically acceptable salts, esters and amides thereof, with the proviso that (a) $R_1$ and $R_2$ are not simultaneously aryl radicals and
(b) when an unsaturated alkylene chain is present which contains a heteroatom, the heteroatom is not connected to an unsaturated aliphatic carbon atom.

The present invention also provides processes for the preparation of these new compounds and pharmaceutical compositions containing them.

19 Claims, No Drawings

CARBOXYLIC ACID DERIVATIVES AND PHARMACEUTICAL COMPOSITIONS AND USES

The present invention is concerned with new carboxylic acid derivatives, with processes for the preparation thereof and with pharmaceutical compositions containing them.

The new carboxylic acid derivatives according to the present invention are compounds of the general formula:

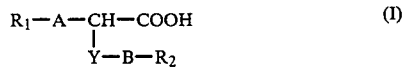  (I)

wherein $R_1$ and $R_2$, which can be the same of different, are optionally substituted aryl radicals or optionally substituted heterocyclic radicals, A is a straight-chained or branched, saturated or unsaturated alkylene chain containing up to 10 carbon atoms, which can contain an oxygen, sulphur or nitrogen atom and is optionally substituted by a hydroxyl group, Y is an $S(O)_n$ group or an oxygen atom, n is 0, 1 or 2 and B is a valency bond or a saturated or unsaturated alkylene radical containing up to 5 carbon atoms, as well as the physiologically acceptable salts, esters and amides thereof, with the proviso that (a) $R_1$ and $R_2$ are not simultaneously aryl radicals and (b) when an unsaturated alkylene chain is present which contains a heteroatom, the heteroatom must not be attached to an unsaturated aiphatic carbon atom.

The compounds of general formula (I) possess valuable pharmacological properties. They can be used as medicaments for the treatment of diabetes, pre-diabetes and especially for the treatment of maturity onset diabetes.

The compounds of general formula (I) have no relationship with known antidiabetic compounds either structurally or in the mode of action. They lower the blood sugar level by increasing the peripheral glucose oxidation. Their action is based upon an increase of the sensitivity of the peripheral tissues towards insulin. In contradistinction to the biguanides, no increase of the blood lactate values is thereby observed. Therefore, the compounds of general formula (I) are also a valuable enrichment in the case of the treatment of the non-diabetic diseased state in which an insulin resistance is present, for example adipositas and atherosclerosis. In addition, they display a marked lipid sinking and can, therefore, also be used for the treatment of metabolic diseases.

As aryl radicals, in all cases there are to be understood aromatic hydrocarbon radicals containing 6 to 14 carbon atoms, the phenyl radical being preferred. These aryl radicals can be substituted one or more times in all possible positions, said substituents being halogen atoms, cyano groups and lower alkyl, lower alkoxy, trifluoromethyl radicals. Alkyl and alkoxy radicals are to be understood to be those containing up to 6 carbon atoms. Preferred in this sense are, for example, methyl, tert.-butyl and methoxy radicals.

By a heterocyclic radical is to be understood a five- or six-membered aromatic ring in which 1 to 3 and preferably 1 carbon atom is replaced by oxygen, sulphur or nitrogen, the thiophene, pyridine and furan radicals being preferred. The heterocyclic radicals can be substituted one or more times in all possible positions by halogen atoms and lower alkyl and lower alkoxy radicals.

In all cases, halogen means fluorine, chlorine or bromine.

Preferred substituents include chlorine atoms and mehthyl, ethyl and methoxy radicals.

For an unbranched alkylene chain A, the following are preferred: $-CH=CHCH_2-$, $-C\equiv CCH_2-$, $-(CH_2)_m-$, $-(CH_2)_r-X-(CH_2)_s-$, $-CH=CHCH_2-X-(CH_2)_t-$ and $-C\equiv CCH_2-X-(CH_2)_t-$, wherein m is a whole number of from 1 to 10, r and s are two whole numbers of from 0 to 10, the sum of which is equal to m, t is a whole number of from 1 to 7 and X is an oxygen, sulphur or nitrogen atom.

As branched alkylene radicals A, there are especially preferred

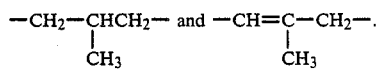

B is a valency bond or an alkylene chain containing up to 5 carbon atoms, the following alkylene chains being preferred: $-CH_2-$, $-(CH_2)_2-$, $-(CH_2)_3-$, $-CH=CH-$, $-CH=CHCH_2-$ and $-CH=C(CH_3)-CH_2-$.

As physiologically acceptable salts, there are especially preferred the alkali metal, alkaline earth metal and ammonium salts, as well as possibly salts with blood sugar-sinking biguanides.

The esters derived from carboxylic acids of general formula (I) contain, as alcohol components, lower monohydroxy alcohols, of which methanol, ethanol and n-butanol are preferred, as well as polyhydroxy alcohols, for example glycerol, or alcohols with other functional groups, for example ethanolamine.

The amides according to the present invention derived from carboxylic acids of general formula (I) contain, as amine components, preferably ammonia, p-aminobenzoic acid, β-alanine, ethanolamine or 2-aminopropanol. However, alkylamines, for example isopropylamine and tert.-butylamine, dialkylamines, for example diethylamine, as well as cyclic amines, for example morpholine and 4-substituted piperazines, can also be used.

The substituted carboxylic acids of general formula (I) possess a centre of chirality. Therefore, the above-given definition of the compounds according to the present invention also includes all possible enantiomers, as well as mixtures and racemates thereof.

The compounds of general formula (I) according to the present invention can be prepared in the following ways:

(A) a compound of the general formula:

  (II)

wherein W is a $-COOR_3$ radical or another group which can be converted into a carboxyl function, $R_3$ is a lower alkyl radical, X here and in the following is a reactive group and Z is a hydrogen atom or an $R_1-A-$ radical, in which $R_1$ and A have the above-given meanings, is reacted in known manner with a compound of the general formula:

  (III)

in which $R_2$, B and Y have the above-given meanings, to give a compound of the general formula:

$$Z-CH-W \atop |\phantom{Z-C}Y-B-R_2,} \quad (IV)$$

in which B, $R_2$, W, Y and Z have the above-given meanings, and optionally subsequently thereto (a) when Y is a sulphur atoms, it is oxidised to an SO or $SO_2$ group, or (b) when Z is a hydrogen atom, either ($b_1$) alkylated with a compound of the general formula:

$$R_1-A-X \quad (V)$$

in which A, $R_1$ and X have the above-given meanings, or ($b_2$) condensed with a compound of the general formula:

$$R_1-A'-CHO \quad (V')$$

in which $R_1$ has the same meaning as above and A' is an alkylene radical A as defined above but shortened by a —$CH_2$— group, and, subsequent to the condensation, the resultant double bond is hydrogenated, or (B) a compound of the general formula:

$$R_1-A-CH-W \atop |\phantom{R_1-A-C}YH} \quad (VI)$$

in which $R_1$, A, W and Y have the above-given meanings, is reacted with a compound of the general formula:

$$R_2-B-X \quad (VII),$$

in which B, $R_2$ and X have the above-given meanings, to give a compound of general formula (IV) and, subsequent to the above reaction step, the compound (IV) obtained is converted into a free carboxyl function or into a physiologically acceptable salt, ester or amide.

The preparation of the starting compounds can take place in known manner, for example by alkylating a malonic ester with a compound of general formula (V) and the compound obtained of the general formula:

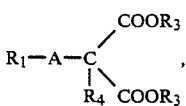  (VIII)

in which A, $R_1$ and $R_3$ have the above-given meanings and $R_4$ is a hydrogen atom, is reacted in known manner to give a compound of general formula (VIII) in which $R_4$ is a reactive group, this is subsequently converted by decarboxylation into a compound of general formula (II), in which W is a —$COOR_3$ group and Z is an $R_1$—A— group, and this is optionally converted into a compound of general formula (VI).

The reaction of the reactive carboxylic acid derivatives of general formula (II) with compounds of general formula (III) preferably takes place with the addition of an acid-binding agent, for example sodium hydrogen carbonate, sodium ethylate or sodium hydride. Esters of the reactive carboxylic acid derivatives are preferably used for the reaction. The reaction can be carried out in an inert solvent, for example diethyl ether, ethanol, benzene, tetrahydrofuran, dioxan or methylene chloride. When using inorganic bases, as reaction medium there can also be used, for example, butan-2-one, dimethylformamide, hexamethylphosphoric acid triamide or acetonitrile. As reactive residue X, there can here be used, for example, a halide or sulphonic acid ester, for example a chloride, or bromide or a p-toluenesulphonyl or methanesulphonyloxy radical.

The oxidation of compounds of general formula (IV), in which Y is a sulphur atom, to give sulphoxides and sulphones, is preferably carried out with hydrogen peroxide in a polar solvent, for example glacial acetic acid, a mixture of glacial acetic acid and acetic anhydride or acetone. Oxidation with trifluoroperacetic acid has proved to be especially advantageous. As solvent, there is hereby preferably used trifluoroacetic acid.

The reaction of reactive derivatives (V) with compounds of general formula (IV), in which Z is a hydrogen atom, and of the reactive derivatives (VII) with compounds of general formula (VI) is preferably carried out with the addition of a strong base, for example sodium methylate, sodium hydride or 1,8-diaza-bicyclo-(5.4.0)-undec-7-ene.

As inert solvents for the reaction, there can be used, for example, ethanol, dimethyl sulphoxide, toluene or benzene. As solvents, there can also be used, for example, dimethylformamide or hexamethylphosphoric acid triamide. The reaction is preferably carried out at ambient temperature or at a moderately elevated temperature or at the boiling temperature of the solvent used. As reactive residues, there can here be used halides or sulphonic acid ester groups, especially chlorides or bromides or the p-toluenesulphonyloxy or methane-sulphonyloxy compounds.

The reaction of the compounds (IV), in which Z is a hydrogen atom, with aldehydes of general formula (V') according to process ($b_2$) takes place under conditions such as are usual for the condensation of activated methylene groups with keto compounds. The condensation is preferably carried out in pyridine or dimethylformamide with the addition of a catalytic amount of a strong base, for example piperidine. An appropriate solvent, for example benzene, is preferably added to the reaction mixture in order to be able to distil off the water of reaction azeotropically.

The subsequent hydrogenation of the resultant double bond is carried out in the usual way with catalytically activated hydrogen at normal pressure or at an elevated pressure. As catalysts, there can be used metal catalysts, for example Raney nicel or palladium-charcoal. As solvents there can be used, for example, acetic acid or lower alcohols and, in the case of carboxylic acids (IV), also aqueous alkali.

By the group W which can be converted into a carboxyl function there is to be understood especially the nitrile group or a residue which can be oxidatively converted into the carboxyl function. As oxidisable group, there are preferably used the hydroxymethyl, the aminomethyl and the formyl radicals or functional derivatives thereof. The oxidation can be carried out with conventional oxidation agents, for example manganese IV compounds, permanganates, dichromates and, in the case of the formyl group, also with atmospheric oxygen and silver oxide.

The conversion of the substituents W possibly to be carried out subsequent to the condensation to give compounds of general formula (IV) takes place, for example, by saponification of carboxylic acid esters to the corresponding carboxylic acids with mineral acids or alkali metal hydroxides in a polar solvent, such as water, methanol, ethanol, dioxan or acetone. The asponification is advantageously carried out with a strong base, such as sodium or potassium hydroxide, in a mixture of methanol and water at ambient temperature or at a moderately elevated temperature. On the other hand, however, the carboxylic acids can also be esterified in the usual way or esters with a particular residue $R_3$ can be converted by transesterification into esters with a different residue $R_3$. The esterification of the carboxylic acids is preferaby carried out in the presence of an acidic catalyst, for example hydrogen chloride, sulphuric acid, p-toluenesulphonic acid or a strong acidic ion exchange resin.

Transesterifications, on the other hand, require the addition of a small amount of a basic substance, for example of an alkali metal or alkaline earth metal hydroxide or of an alkali metal alcoholate. For the esterification of the carboxyl group or for a transesterification, there can, in principle, be used all alcohols. However, it is preferred to use lower monohydroxy alcohols, for example methanol, ethanol or propanol, as well as polyhydroxy alcohols, for example glycerol, or alcohols with other functional groups, for example ethanolamine.

The amides according to the present invention derived from the carboxylic acids of general formula (I) are preferably prepared according to known methods from the carboxylic acids or from reactive derivatives thereof, for example carboxylic acid halides, esters, azides, anhydrides or mixed anhydrides, by reaction with amines. As amine components, there can be used, for example, ammonia, alkylamines and dialkylamines but also aminoalcohols, for example ethanolamine and 2-amino-propanol, as well as amino acids, for example p-amino-benzoic acid, β-alanine and the like. Other valuable amine components include alkyl-, aralkyl- and aryl-piperazines.

The preparation of the above amides can also take place by partial saponification of nitriles derived from carboxylic acids according to the present invention. The saponification takes place in dilute mineral acids at moderately elevated temperatures, in alkaline hydroperoxide solution or advantageously in 98% sulphuric acid or polyphosphoric acid.

For the preparation of salts with pharmacologically acceptable organic and inorganic bases, for example sodium hydroxide, potassium hydroxide, calcium hydroxide, ammonium hydroxide, methylglucamine, morpholine or ethanolamine, the carboxylic acids can be reacted with the appropriate bases. Mixtures of the carboxylic acids with an appropriate alkali metal carbonate or hydrogen carbonate can also be considered.

For the preparation of pharmaceutical compositions, the compounds of general formula (I) are mixed in known manner with appropriate pharmaceutical carrier substances, aroma, flavouring and colouring materials and formed, for example, as tablets or dragees or, with the addition of appropriate adjuvants, suspended or dissolved in water or an oil, for example olive oil.

The compounds of general formula (I) can be administered orally or parenterally in liquid or solid form. As injection medium, water is peferably used which contains the stabilising agents, solubilising agents and/or buffers usual in the case of injection solutions. Additives of this kind include, for example, tartrate and borate buffers, ethanol, dimethyl sulphoxide, complex formers (such as ethylenediamine-tetraacetic acid), high molecular weight polymers (such as liquid polyethylene oxide) for viscosity regulation or polyethylene derivatives of sorbit anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, the state of health and the weight of the recipient, the extent of the disease, the nature of other treatments possibly carrie out simultameously, the frequency of the treatments and the nature of the desired action. The diaily dose of the active compound in usually 0.1 to 50 mg./kg. body weight. Normally, 0.5 to 40 and preferably 1.0 to 20 mg./kg./day in one or more administrations per day are sufficient to achieve the desired results.

Preferred in the meaning of the present invention are, apart from the compounds of general formula (I) mentioned in the examples, as well as the esters and amides thereof, also the following compounds:

7-phenyl-2-(2-thienylsulphonyl)-heptanoic acid
7-(4-methylphenyl)-2-(2-thienylsulphonyl)-heptanoic acid
7-(4-methoxyphenyl)-2-(2-thienylsulphonyl)-heptanoic acid
7-(4-chlorophenoxy)-2-(2-thienylsulphonyl)-heptanoic acid
4-[2-(4-chlorophenyl)-ethoxy]-2-(2-thienylsulphonyl)-butyric acid
5-(4-chlorophenyl)-2-(2-thienylsulphonyl)-4-pentinic acid
8-(4-chlorophenyl)-2-(2-thienylsulphonyl)-octanoic acid
7-(4-chlorophenyl)-2-(2-thienylthio)-heptanoic acid
7-(4-chlorophenyl)-2-(2-thienyloxy)-heptanoic acid
7-(4-chlorophenylthio)-2-(2-thienyloxy)-heptanoic acid
7-(4-chlorophenylamino)-2-(2-thienylsulphonyl)-heptanoic acid
7-(4-chlorophenyl)-2-(2-methyl-3-furanylthio)-heptanoic acid
7-(4-chlorophenyl)-2-(1-methyl-2-imidazolyl)-heptanoic acid
7-(4-chlorophenyl)-2-(2-pyridylthio)-heptanoic acid
7-(4-chlorophenyl)-2-(4-pyridylthio)-heptanoic acid
7-(4-chlorophenyl)-2-(3-pyridylsulphonyl)-heptanoic acid
8-(2-thienyl)-2-(4-methylphenoxy)-octanoic acid
8-(2-thienyl)-2-(4-methylphenylthio)-octanoic acid
8-(2-thienyl)-2-(phenylsulphonyl)-octanoic acid
8-(2-thienyl)-2-(4-tert.-butylphenylsulphonyl)-octanoic acid
8-(2-thienyl)-2-(4-fluorophenylsulphonyl)-octanoic acid
8-(2-thienyl)-2-(4-chlorophenylsulphonyl)-octanoic acid
8-(2-thienyl)-2-(3-trifluoromethylphenylsulphonyl)-octanoic acid 8-(2-thienyl)-2-(4-methoxyphenylsulphonyl)-octanoic acid
8-(2-thienyl)-2-(2-phenylethylsulphonyl)-octanoic acid
8-(2-thienyl)-2-(4-methylphenylsulphinyl)-octanoic acid
8-(2-furanyl)-2-(4-methylphenylsulphonyl)-octanoic acid
8-(2-thienyl)-2-(2-phenylethenylsulphonyl)-octanoic acid
8-(2-thienyl)-2-(4-chlorocinnamylsulphonyl)-octanoic acid
8-(3-thienyl)-2-(4-methylphenylsulphonyl)-octanoic acid
8-(5-methyl-2-thienyl)-2-(4-methylphenylsulphonyl)-octanoic acid
8-(5-chloro-2-thienyl)-2-(4-methylphenylsulphonyl)-octanoic acid
8-(3-methoxy-2-thienyl)-2-(4-methylphenylsulphonyl)-octanoic acid
8-(2-thienyl)-2-2-(4-methylphenylsulphinyl)-octanoic acid
8-(4-pyridyl)-2-(4-methylphenylsulphonyl)-octanoic acid
8-(3-pyridyl)-2-(4-methylphenylsulphonyl)-octanoic acid
8-(2-pyridyl)-2-(4-methylphenylsulphonyl)-octanoic acid
8-(4-ethyl-2-pyridyl)-2-(4-methylphenylsulphonyl)-octanoic acid
7-(3-methyl-2-pyridyl)-8-hydroxy-2-(4-methylphenylsulphonyl)-heptanoic acid
7-(3,5-dimethyl-4-oxazolyl)-2-(4-methylphenylsulphonyl)-heptanoic acid.

The following examples are given for the purpose of illustrating the present invention:

EXAMPLE 1

2-(4-Methylphenylsulphonyl)-8-(2-thienyl)-octanoic acid

A solution of 28 mmole sodium ethylate (prepared from 0.644 g. sodium) in 70 ml. anhydrous ethanol is mixed, while stirring, with a solution of 6.78 g (28 mmole) ehtyl 4-methylphenylsulphonylacetate in 150 ml. anhydrous ethanol and heated at reflux temperature for 1 hour. 7.0 g. (28 mmole) 6-(2-thienyl)-hexyl bromide in 20 ml. anhydrous ethanol are then added dropwise thereto and the mixture again heated under reflux for 6 hours. Subsequently, the reaction mixture is evaporated, the residue is taken up in water and the mixture extracted with diethyl ether. The ethereal extracts are dried and evaporated. The residue is chromatographed with a mixture of heptane and butan-2-one (2:1 v/v) on silica gel, there being obtained 8.4 g. (73% of theory) ethyl 2-(4-methylphenylsulphonyl)-8-(2-thienyl)-octanoate in the form of a colourless oil.

3.3 g. (8 mmole) of this ester are stirred for 6 hours at ambient temperature in a mixture of 8.5 ml. 1N aqueous potassium hydroxide solution and 50 ml. methanol. The methanol is then distilled off and the residue is diluted with water and washed with diethyl ether. The aqueous phase is clarified with charcoal, acidified and the oil which separates out is extracted with diethyl ether. As residue, there are obtained 3.0 g of a colourless oil. The oil is stirred with a solution of 0.65 g. (7.8 mmole) sodium hydrogen carbonate in 20 ml. water until a clear solution is formed. This is then evaporated, there being obtained, as residue, 2.6 g. (81% of theory) sodium 2-(4-methylphenylsulphonyl)-8-(2-thienyl)-octanoate; m.p. 129°-131° C.

The 6-(2-thienyl)-hexyl bromide used as starting material can be obtained from 6-oxo-6-(2-thienyl)-hexanoic acid (see Papa and Schwenk, J.A.C.S., 69, 3022) in the following manner:

A mixture of 30.0 g. (0.14 mole) 6-oxo-6-(2-thienyl)-hexanoic acid (m.p. 77° C.), 26.3 g. (0.47 mole) potassium hydroxide, 17.5 ml. (0.35 mole) hydrazine hydrate, 4 ml. water and 180 ml. diethyleneglycol is heated to reflux temperature for 2 hours. The diethyleneglycol is then distilled off with the use of a descending cooler, the residue is taken up in water and the neutral part washed out with diethyl ether. The aqueous phase is subsequently acidified and extracted with diethyl ether. The ethereal extracts are dried and evaporated. The residue is distilled in a vacuum to give 16.1 g. (58% of theory) 6-(2-thienyl)-hexanoic acid; b.p. 135°-137° C./0.4 mbar.

A suspension of 7.6 g. (0.2 mole) lithium aluminium hydride in 200 ml. anhydrous diethyl ether is mixed, while stirring, with a solution of 16 g. (80 mmole) of this carboxylic acid in 100 ml. anhydrous diethyl ether and the mixture further stirred for 2 hours without cooling and then for 1 hour under reflux. The reaction mixture is subsequently mixed with water and the organic phase evaporated. As residue, there are obtained 14.7 g. (98% of theory) 6-(2-thienyl)-hexanol in the form of a colourless oil.

20 g. (0.108 mole) of this hexanol are cooled with ice and mixed dropwise with 29.3 g. (0.108 mole) phosphorus tribromide. The reaction mixture is further stirred for 1 hour with ice cooling and then for 4 hours at 100° C. and poured on to ice. The mixture is extracted with diethyl ether and the extracts evaporated. The residue is distilled in a vacuum to give 15.3 g. (57% of theory) 6-(2-thienyl)-hexyl bromide; b.p. 115°-117° C./0.2 mbar.

EXAMPLE 2

7-(4-chlorophenyl)-2-(2-thienylsulphonyl)-heptanoic acid

To a solution of 40 mmole sodium ethylate (prepared from 0.92 g. sodium) in 75 ml. anhydrous ethanol are successively added, while stirring, 9.37 g. (40 mmole) ethyl (2-thienyl)-sulphonylacetate in 35 ml. ethanol and 10.46 g (40 mmole) 5-(4-chlorophenyl)-pentyl bromide in 30 ml. ethanol. The reaction mixture is subsequently heated to reflux temperature for 6 hours, then evaporated and the residue taken up in diethyl ether. The ethereal solution is washed with water, dried and evaporated. The residue is chromatographed on silica gel with methylene chloride. There are obtained 8.6 g. (52% of theory) ethyl 7-(4-chlorophenyl)-2-(2-thienyl)-heptanoate; m.p. 64°-66° C. 7.3 g. (17.5 mmole) of this ester are stirred for 2 hours at 40° C. in a mixture of 40 ml. 1N aqueous potassium hydroxide solution and 120 ml. methanol. The methanol is then distilled off and the residue is diluted with water and washed with diethyl ether. Subsequently, the aqueous solution is clarified with charcoal and acidified. The precipitate obtained is taken up in diethyl ether and the ethereal solution is dried and evaporated, there being obtained 6.5 g. (96% of theory) 7-(4-chlorophenyl)-2-(2-thienylsulphonyl)-heptanoic acid; m.p. 106°-108° C.

The ethyl (2-thienyl)-sulphonylacetate used as starting material can be obtained from lithium (2-thienyl)- sulphinate and ethyl bromoacetate in the form of a colourless oil. Yield 78% of theory; b.p. 156°–157° C./0.2 mbar.

It will be understood that the specification and examples are illustrative but not limitative of the present invention and that other embodiments within the spirit and scope of the invention will suggest themselves to those skilled in the art.

TEST REPORT

To show the blood glucose lowering action of the compounds of formula I the following experiments were performed:

In each case, groups of ten genetically diabetic OB-/OB-mice were administered once per day the test substance for 5 days in a dosage of 100 ml/kg p. o. in tylose suspension. At the beginning of the experiment the average values of the glucose concentration in blood were identical within each group. A reference group of animals was given tylose p. o. only. During the whole period of the experiments the animals were given food and water ad libitum. Before the first administration of the substance and after the last administration, 0.01 ml blood were withdrawn from the tail veine. The determination of blood glucose was performed using the hexokinase method in haemolysate.

The therapeutic action of a test substance was characterized by its lowering effect on blood glucose (given in percent), taking into consideration the glycaemia of the reference group.

TABLE

| Compound of Example | blood glucose lowering effect in % |
|---|---|
| 1 | −24 |
| 2 | −40 |

What is claimed:

1. A carboxylic acid compound of the formula:

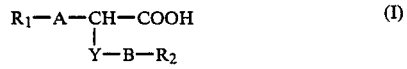

wherein
$R_1$ and $R_2$ which can be the same or different are a substituted or unsubstituted $C_6$–$C_{14}$ aryl or are a substituted or unsubstituted thiophene and wherein said aryl substituents are fluorine, chlorine, bromine, a cyano group, $C_1$–$C_6$ alkyl, $C_1$–$C_6$ alkoxy or a trifluoromethyl and wherein said thiophene substituents are fluorine, chlorine, bromine, $C_1$–$C_6$ alkyl or $C_1$–$C_6$ alkoxy,
A is a straight or branched saturated or unsaturated $C_1$–$C_{10}$ alkylene chain which chain can contain an oxygen, sulphur or nitrogen and is optionally substituted by a hydroxyl group,
Y is an S(O)n group or an oxygen,
n is 0, 1 or 2,
B is a valency bond or a saturated or unsaturated $C_1$–$C_5$ alkylene,
and the physiologically active salts, esters and amides thereof and the enantiomers, mixtures and racemates thereof,
with the exception that $R_1$ and $R_2$ cannot both be aryl and when an unsaturated alkylene chain is present which contains a heteroatom, the heteroatom is not connected to an unsaturated aliphatic carbon.

2. The carboxylic acid compound of claim 1 wherein $R_1$ or $R_2$ is phenyl.

3. The carboxylic acid compound of claim 1 wherein the alkyl or alkoxy substituent on the aryl or thiophene of $R_1$ or $R_2$ is methyl, tert.-butyl or methoxy.

4. The carboxylic acid compound of claim 1 wherein the thiophene substituents are chlorine, methyl, ethyl or methoxy.

5. The carboxylic acid compound of claim 1 wherein the unbranched alkylene chain A is selected from the group consisting of
—CH=CHCH$_2$—, —C≡CCH$_2$—,
—(CH$_2$)$_m$—, —(CH$_2$)$_4$—X—(CH$_2$)$_s$—,
—CH=CHCH$_2$—X—(CH$_2$)$_r$— and
—C≡CCH$_2$—X—(CH$_2$)$_r$—,
wherein m is a whole number from 1–10, r and s are two whole numbers from 0–10, the sum of which is equal to m, t is a whole number from 1 to 7 and X is oxygen, sulphur nor nitrogen.

6. The carboxylic acid compound of claim 1 wherein the branched alkylene chain A is

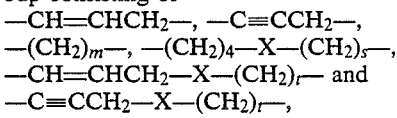

7. The carboxylic acid compound of claim 1 wherein the alkylene chain of B is selected from the group consisting of —CH$_2$—, —(CH$_2$)$_2$—, —(CH$_2$)$_3$—, —CH=CH—, —CH=CHCH$_2$— and —CH=C(CH$_3$)—CH$_2$—.

8. A carboxylic compound of the formula 2-(4-methylphenylsulphonyl)-8-(2-thienyl)-octanoic acid and the physiologically active ester, amide or salt thereof and the racemate or enantiomer thereof.

9. A carboxylic compound of the formula 7-(4-chlorophenyl)-2-(2-thienylsulfonyl)-heptanoic acid and the physiologically active ester, amide or salt thereof and the racemate or enantiomer thereof.

10. A pharmaceutical composition for the treatment of diabetes, adipositas or atherossclerosis wherein said composition contains a pharmaceutically effective amount of at least one of the compounds of any one of claims 1–7 in a pharmaceutically acceptable carrier.

11. A pharmaceutical composition for the treatment of diabetes, adipositas or atherosclerosis wherein said composition contains a pharmaceutically effective amount of the compound of claim 8 in a pharmaceutically acceptable carrier.

12. A pharmaceutical composition for the treatment of diabetes, adipositas or atherosclerosis wherein said composition contains a pharmaceutically effective amount of the compound of claim 9 in a pharmaceutically acceptable carrier.

13. A method for the treatment of diabetes, adipositas or atherosclerosis comprising administering to a patient in need of said treatment an effective amount of at least one of a pharmaceutically acceptable compound of any one of claims 1–7.

14. A method for the treatment of diabetes, adipositas or atherosclerosis comprising administering to a patient in need of said treatment an effective amount of a pharmaceutically acceptable compound of claim 8.

15. A method for the treatment of diabetes, adipositas or atherosclerosis comprising administering a to patient in need of said treatment an effective amount of a pharmaceutically acceptable compound of claim 11.

16. The method of claim 13, wherein the effective amount is 0.1 to 50 mg/kg body weight per day.

17. The method of claim 13, wherein the effective amount is 1.0 to 20 mg/kg body weight per day.

18. The method of claim 14 or 15 wherein the effective amount is 0.1 to 50 mg/kg body weight per day.

19. The method of claim 14 or 15 wherein the effective amount is 1.0 to 20 mg/kg body weight per day.

* * * * *

UNITED STATES PATENT AND TRADEMARK OFFICE
CERTIFICATE OF CORRECTION

PATENT NO. : 4,833,161                                          Page 1 of 2
DATED      : May 23, 1989
INVENTOR(S): Hans P. Wolff, et al.

It is certified that error appears in the above-identified patent and that said Letters Patent is hereby corrected as shown below:

Col. 1, line 17:        delete "of" and insert -- or --.

Col. 1, line 32:        delete "aiphatic" and insert
-- aliphatic --.

Col. 2, line 6:         delete "mehthyl" and insert -- methyl --.

Col. 5, line 7:         delete "asponification" and insert
-- saponification --.

Col. 6, line 21:        delete "carrie" and insert -- carried --.

Col. 7, line 35:        delete "illustratihg" and insert
                        -- illustrating --.

Col. 7, line 44:        delete "ehtyl" and insert -- ethyl --.

Col. 10, line 13
    Claim 5    :        delete "-(CH$_2$)$_4$-X-" and insert

-- -(CH$_2$)$_r$-X- --.

Col. 10, line 42
    Claim 10   :        delete "atherossclerosis" and insert
                        -- atherosclerosis --.

UNITED STATES PATENT AND TRADEMARK OFFICE
CERTIFICATE OF CORRECTION

PATENT NO. : 4,833,161

DATED : May 23, 1989

INVENTOR(S) : Hans P. Wolff, et al.

It is certified that error appears in the above-identified patent and that said Letters Patent is hereby corrected as shown below:

Col. 10, line 68
    Claim 15     :    delete "11" and insert -- 9 --.

Signed and Sealed this

Twenty-second Day of May, 1990

Attest:

HARRY F. MANBECK, JR.

*Attesting Officer*     *Commissioner of Patents and Trademarks*